United States Patent [19]

Freeman et al.

[11] Patent Number: 5,965,717
[45] Date of Patent: Oct. 12, 1999

[54] ORGANIC PIGMENTS FROM TWISTED BENZIDINES

[75] Inventors: Harold S. Freeman, Raleigh, N.C.; David Hinks, Spartanburg, S.C.; Jolanta Sokolowska-Gajda, Raleigh, N.C.

[73] Assignee: North Carolina State University, Raleigh, N.C.

[21] Appl. No.: 08/963,963

[22] Filed: Nov. 4, 1997

[51] Int. Cl.$^6$ ...................... C07C 245/08; C07C 255/17; C07D 403/12; C07D 235/26
[52] U.S. Cl. .......................... 534/823; 534/825; 855/296; 548/365; 548/305.4; 558/394
[58] Field of Search ..................................... 534/823, 825; 544/296; 548/365, 305.4; 558/394

[56] References Cited

U.S. PATENT DOCUMENTS

| | | | |
|---|---|---|---|
| 3,567,707 | 3/1971 | Neave et al. | 260/161 |
| 4,211,875 | 7/1980 | Genshaw et al. | 435/14 |
| 4,297,502 | 10/1981 | Hermann et al. | 560/35 |
| 4,322,554 | 3/1982 | Hermann et al. | 564/273 |
| 4,987,258 | 1/1991 | Hunger et al. | 564/309 |
| 5,180,817 | 1/1993 | Orgino et al. | 534/811 |

FOREIGN PATENT DOCUMENTS

| | | |
|---|---|---|
| 3511544 A1 | 10/1986 | Germany . |
| 3511545 A1 | 10/1986 | Germany . |
| 3534634 A1 | 4/1987 | Germany . |

OTHER PUBLICATIONS

Holland et al., "A Safer Substitute for Benzidine in the Detection of Blood", Tetrahedron, vol. 30, (1974), pp. 3299–3302.

Fishbein, "Aromatic Amines", *The Handbook of Environmental Chemistry*, vol.3, Part C., (1984), pp. 1–40.

Holland, V. R. et al., A safer Substitute for Benzidine in the Detection of Blood, Tetrahedron, vol. 30, 3299–3302, Jan. 1974.

*Primary Examiner*—Floyd D. Higel
*Assistant Examiner*—Dominic Keating
*Attorney, Agent, or Firm*—Jenkins & Wilson, P.A.

[57] ABSTRACT

Nonmutagenic, highly twisted derivatives of benzidine of the following formula

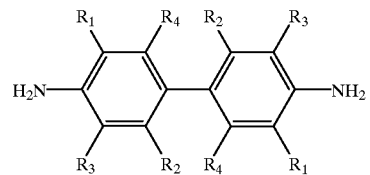

useful as intermediates for the preparation of various organic pigments were obtained. The benzidine derivatives are significantly rotated about the biphenyl linkage due to bulky substituents at the $R_2$ and/or $R_4$ positions. Bisazomethine, disaoacetoacetanilide, disazopyrazolone, disazobenzimidazolone and disazonaphthol pigments prepared from these highly twisted benzidines exhibit hypsochromic spectral shifts relative to pigments prepared from other benzidine compounds with less twist about the biphenyl linkage, for instance, other benzidine compounds in which all four $R_2$ and $R_4$ represent H. Greenish-yellow, yellow, orange, red and brown pigments obtained from the twisted benzidines are nonmutagenic in the standard Ames test and Prival modification.

16 Claims, No Drawings

ORGANIC PIGMENTS FROM TWISTED BENZIDINES

TECHNICAL FIELD

The present invention generally relates to intermediates for use in the preparation of organic pigments. More specifically, this invention relates to an approach to the development of novel, nonmutagenic derivatives of benzidine that are highly twisted about the biphenyl linkage and useful for the preparation of organic pigments. A large dihedral angle about the biphenyl linkage, provides for using the novel, nonmutagenic derivatives of benzidine to prepare organic pigments with hypsochromic shifts relative to pigments prepared from derivatives of benzidine compounds with a small dihedral angle about the biphenyl linkage.

BACKGROUND OF THE INVENTION

It is well known that bis-chromophoric dyes and pigments (e.g. disazo compounds) prepared from unsubstituted or 3,3'-disubstituted benzidines exhibit bathochromic spectral shifts relative to identically substituted mono-chromophoric colorants (e.g. monoazo compounds) prepared from aniline, or 2-substituted derivatives thereof. For example, in two papers by Christie et al. (*Dyes Pigm.*, 9 (1988) 37–56; *Dyes Pigm.*, 11 (1989) 109–121), a diarylide pigment (see, compound 1) exhibited a $\lambda_{max}$ of 445 nm in N,N-dimethylformamide (abbreviated as DMF) while the corresponding monoarylide pigment (see, compound 2) exhibited a $\lambda_{max}$ of 392 nm in DMF.

In the case of azo pigments derived from acetoacetanilide, monoarylide pigments (e.g., compound 2) are characterized by good light fastness and poor solvent resistance. Diarylide pigments (e.g., compound 1), however, possess higher color strength, good thermal stability, and enhanced solvent resistance compared to the monoarylide pigments. Thus, diarylide pigments are the preferred class of colorants for many applications.

However, the significant bathochromic shift observed when benzidine-type intermediates are employed in the preparation of diarylide pigments (relative to when aniline-type compounds are used for the synthesis of monoarylide pigments) can limit the color gamut of diarylides. In particular, greenish-yellow dyes and pigments are not easily accessible. Thus, the ability to prepare colorants based on derivatives of benzidine that exhibit hypsochromic shifts to those normally achievable is desirable.

With respect to diarylide and monoarylide pigments, if it is presumed that diarylides exhibit bathochromic shifts relative to analogous monoarylides due to, in the most part, significant Π orbital overlap across the biphenyl linkage at the 1,1'-position, where the numbering of the benzidine positions is as follows

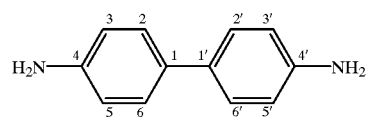

then, it follows that hypsochromic shifts should be obtainable by decreasing the Π orbital overlap.

One method by which a reduction in the degree of Π orbital overlap could be achieved is by twisting of the biphenyl group about the 1,1'-bond, for example, by insertion of bulky substituents in the 2,2'-positions. Examination of the open literature (see, for instance, J. Lenoir, *The*

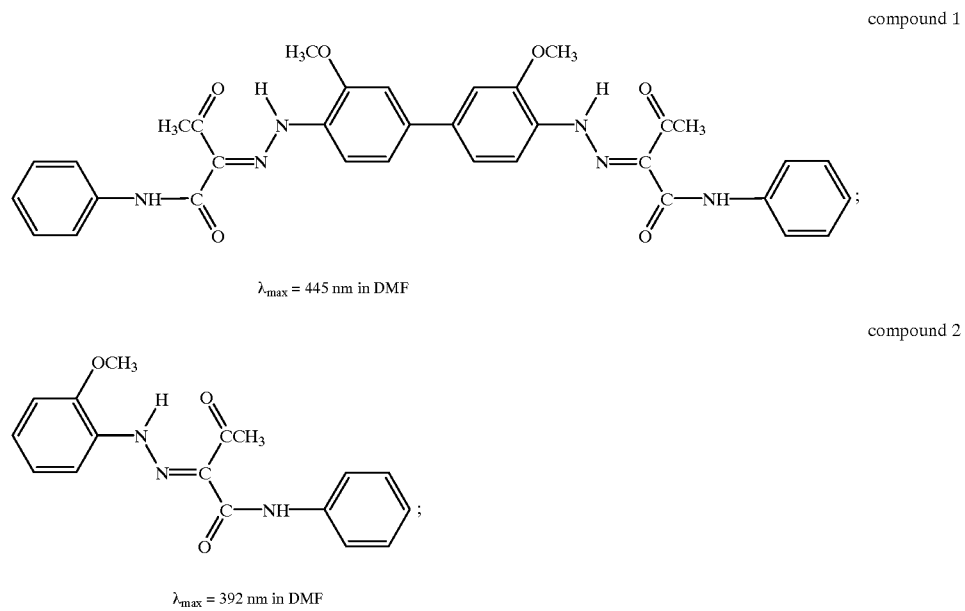

Chemistry of Synthetic Dyes, Volume V, ed. K. Venkataraman, Academic Press, New York (1952) 345) shows that an example of a diarylide pigment containing a substituent other than hydrogen in the 2,2'-positions has been reported. The example is compound 3 (C.I. Pigment Yellow 15). Compound 4 (C.I. Pigment Yellow 81) and compound 5 (C.I. Pigment Yellow 113) are two other examples from the Colour Index (3rd Ed., Lund-Humphries: London, 1971). See Table 1 below for these three structures.

TABLE 1

Selected diarylide pigments derived from twisted benzidines

[Chemical structure diagram showing a symmetric diarylide pigment with substituents $R_1$, $R_2$, $X_1$, $X_2$, $X_3$]

| Compound | $R_1$ | $R_2$ | $X_1$ | $X_2$ | $X_3$ |
|----------|-------|-------|-------|-------|-------|
| 3 | OMe | Cl | Me | Me | H |
| 4 | Cl | Cl | Me | Me | H |
| 5 | Cl | Cl | Me | Cl | H |
| 6 | Cl | H | Me | Cl | H |

Compounds 3, 4, and 5 are indeed hypsochromic relative to analogous pigments in which the substituent at each position $R_2$ is hydrogen. For instance, compound 6 (C.I. Pigment Orange 14) is orange, whereas compound 5 is yellow.

Although the inclusion of a bulky substituent into the 2,2'-positions of benzidine-type compounds has been undertaken, thereby providing a hypsochromic shift in the resultant colorant, previously made compounds are believed to be genotoxic, and are therefore potentially hazardous to humans and the environment. By genotoxic is meant these compounds interact with DNA to produce heritable changes in a cell or organism. In humans, such changes are associated with birth defects, carcinogenesis, and other types of diseases.

It is well documented in the open literature that benzidine and certain well-known derivatives of benzidine, for instance, 3,3'-dichlorobenzidine, 3,3'-dimethylbenzidine and 3,3'-dimethoxybenzidine, hereinafter referred to as common benzidines, are mutagenic. It is also known that certain colorants prepared from common benzidines are mutagenic. Furthermore, it is generally believed that compounds that exhibit mutagenic activity are potentially carcinogenic, and that the manufacture and use of such substances presents an occupational risk, as well as a potential risk to the health of living organisms that are exposed to those substances.

Following the discovery of the genotoxicity of benzidine, and later the mutagenicity of common benzidines, legislation was introduced in many countries either banning or severely restricting the industrial production and use of these compounds (see, for instance, OSHA. Carcinogens: Occupational Health and Safety Standards; U.S. Federal Register 39 (1974) 3756–3797, and The Carcinogenic Substances Regulations 1967, U.K. Statutory Instrument No. 879). For a discussion of the genotoxicity of benzidine and its congeners, see, for instance, Clarke (*Int. Dyer & Text. Printer*, No. 5, 250–255) and Fishbein (*The Handbook of Environmental Chemistry*, Vol. 3, Part C, Ed. by O. Hutzinger, Springer-Verlag, New York (1984) 1–40).

The restricted synthesis and use of common benzidines has resulted in a large reduction in their employment in the field of coloration, as well as other fields such as polymer cross-linking and clinical analysis. Production of high volume dyes based on benzidine itself and its congeners has been practically discontinued in the Western World.

In certain countries, however, the use of pigments derived from common benzidines is permitted, since pigments tend to be unchanged during normal processing conditions, and since prolonged exposure of living organisms to pigments derived from common benzidines has not been shown to result in significant genotoxicity. Hence, pigments derived from common benzidines, particularly 3,3'-dichlorobenzidine, are still available commercially. In fact, diarylide pigments derived from 3,3'-dichlorobenzidine command the major market share of organic yellow pigments.

Nevertheless, the occupational risk remains for manufacturing common benzidines themselves prior to their conversion into pigments. There is a risk also of small amounts of common benzidines in their unconverted form becoming incorporated into pigments, and therefore being released into receiving waters following pigment processing. Furthermore, there is a risk of common benzidines being released upon thermal degradation of pigments derived from common benzidines following certain processing conditions, such as melt extrusion of pigment-colored polymers.

An examination of the pertinent literature prior to the discovery of the genotoxicity of benzidine reveals the commercial importance of dyes and pigments prepared from common benzidines. Approximately 250 colorants derived from benzidine, approximately 90 colorants derived from 3,3'-dimethoxybenzidine (o-dianisidine), and approximately 95 colorants derived from 3,3'-dimethylbenzidine (o-tolidine) are listed in the Colour Index (3rd Ed., Lund-Humphries: London, 1971). The commercial importance of common benzidines was due in part to the economy and ease with which such compounds could be produced, and also to the desirable technical properties the aforementioned compounds can impart to a colorant.

In view of the commercial importance of common benzidines prior to the discovery of their harmful effects to living organisms, the prospect remains that production of such compounds could be restored to the marketplace on a wider scale should a method be found that significantly reduces the harmful effects of benzidine-type compounds. In recent years, researchers have worked towards the development of nonmutagenic amines, since mutagenicity is correlated with carcinogenicity. In addition, in vitro test methods have been developed to assess the mutagenic activity of compounds as a means of predicting carcinogenicity.

The most widely accepted mutagenicity screening test procedure for amines is the *Salmonella mammalian* microsome mutagenicity assay developed by Ames et al. (*Mutat. Res.*, 31 (1975) 347), hereinafter referred to as the Ames test. Subsequently, a modification of the Ames test was introduced by Prival et al. (*Mutat. Res.*, 97 (2) (1982) 103) specifically for evaluating the mutagenicity of azo compounds, hereinafter referred to as the Prival modification. For a general discussion of mutagenicity as it pertains to colored materials, see, for instance, Freeman et al., Genotoxicity of Azo Dyes: Bases and Implications, Physico-Chemical Principles of Color Chemistry, Advances in Color Chemistry Series, Vol. 4, ed. by A. T. Peters and H. S. Freeman (Blackie Academic Press: Glasgow, 1996) 254–291; Freeman et al., *Dyes Pigm.* 8 (6) (1987) 431–47; and Freeman et al., *CHEMTECH*, July (1991), 438–445.

The discovery by Shahin et al. (*Mutation. Res.* 79 (1980) 289; *Environ. Mutagen.* 7 (4) (1985) 535) that the mutagenicity of aromatic amines can be lowered or removed by incorporating bulky alkyl or alkoxy substituents ortho to the amino group on a molecule has spurred significant interest in this area, particularly for a method to prepare nonmutagenic derivatives of benzidine.

In one patent, DE 3 511 544 A1 to Hunger et al., described is the synthesis of nonmutagenic derivatives of benzidine of the following formula

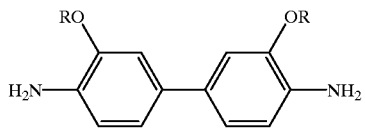

wherein R represents n-butyl, isopentyl, or phenyl. These compounds were reported to be nonmutagenic in the Ames test, presumably due to the ability of bulky substituents in the two ortho positions to the two amino groups in the 4,4'-positions to prevent metabolic activation.

In another patent, DE 3 511 545 A1 to Hunger et al., described is the synthesis of derivatives of benzidine of the following formula

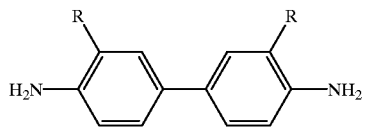

wherein R represents n-propyl, isopropyl, n-butyl, isobutyl, 1-methylpropyl, n-propoxy, isopropoxy, isobutoxy, 1-methylpropoxy, or 2-methoxyethoxy. These compounds were reported to be nonmutagenic in the Ames test.

In a later patent, DE 3 534 634 A1 to Bauer et al., nonmutagenic compounds of the type described by Hunger et al. were used as intermediates for the synthesis of water soluble disazo dyes of the following formula

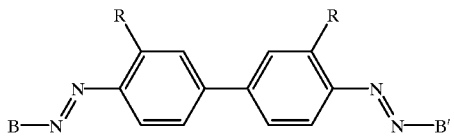

wherein R represents groups as described in the two patents to Hunger et al., and B and B' represent, for instance, substituted naphthalene groups of the following formula

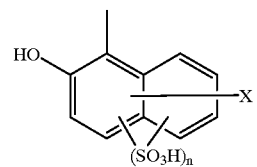

wherein X represents, for instance, OH, or $NH_2$, and n represents 0, 1, or 2.

Furthermore, utilization of a nonmutagenic derivative of benzidine is described in Holland et al. (Tetrahedron, 30, No. 18 (1974) 3299–3302) and also in U.S. Pat. No. 4,211,845 to Conshaw et al. In both instances, a benzidine derivative of the following formula

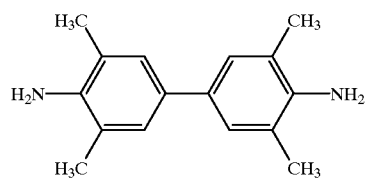

is employed as a reagent for detecting the presence of, for example, glucose in fluids. The compound, 3,5,3',5'-tetramethylbenzidine, is nonmutagenic in the Ames test.

A different approach that has been taken to reduce the occupational risk of colorants derived from benzidines involves the preparation of dyestuff intermediates that provide technical properties similar to the common benzidines, while exhibiting low genotoxicity. An example of this approach is shown in U.S. Pat. No. 5,180,817 to Ogino et al., which discloses compounds having, for instance, the following formula

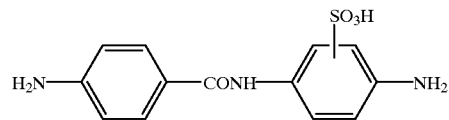

as replacements for benzidine.

Despite the aforementioned methods for the generation of nonmutagenic derivatives of benzidine, examination of the open literature shows that benzidine-type compounds have not been disclosed that contain bulky alkyl, alkoxy, aryloxy, and/or halogeno substituents ortho to the amino functional groups and substituents ortho to the biphenyl linkage, the former providing nongenotoxicity and the latter also providing colorants giving hypsochromic shifts.

SUMMARY AND OBJECTS OF THE INVENTION

Accordingly, the present invention provides a nonmutagenic, highly twisted benzidine derivative and acid salts thereof, wherein the derivative has (1) two phenyl rings with a biphenyl linkage therebetween, (2) a first and a second amino functional moiety with the first amino moiety on one phenyl ring para to the biphenyl linkage and the second amino moiety on the other phenyl ring para to the biphenyl linkage, and (3) at least four substituents on the two phenyl rings, wherein the substituents are selected from the group consisting of alkyl, alkoxy, hydroxyalkyl, alkoxyalkyl, aryloxy, and halogeno substituents, and mixtures thereof, with (A) one each of two of the same alkyl, alkoxy, hydroxyalkyl, alkoxyalkyl, and aryloxy substituents present ortho respectively to each of the two amino functional groups, provided that the alkyl, alkoxy, hydroxyalkyl, and alkoxyalkyl each has a minimum of three carbons, and (B) one each of two of the same alkyl, alkoxy, hydroxyalkyl, alkoxyalkyl, aryloxy, and halogeno substituents present ortho respectively to each side of the biphenyl linkage, provided that the alkyl, alkoxy, hydroxyalkyl, and alkoxyalkyl each has a maximum of four carbons, and wherein component (A) and component (B) are para to each other for each of the two pairs of component (A) and component (B).

Also, the present invention provides nonmutagenic, highly twisted benzidine derivatives and acid salts thereof, wherein the benzidine derivatives are of the formula

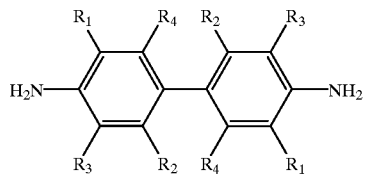

wherein
each $R_1$ is the same and represents $C_{3-6}$-alkyl, $C_{3-6}$-alkoxy, $C_{3-6}$-hydroxyalkyl, $C_{3-6}$-alkoxyalkyl, or aryloxy, and
each $R_2$ is the same and represents halogen, $C_{1-4}$-alkyl, $C_{1-4}$-alkoxy, $C_{1-4}$-hydroxyalkyl, $C_{1-4}$-alkoxyalkyl, or aryloxy, and
each $R_3$ is the same and represents H or $CH_3$, and
each $R_4$ is the same and represents H, halogen, $C_{1-4}$-alkyl, $C_{1-4}$-alkoxy, $C_{1-4}$-hydroxyalkyl, $C_{1-4}$-alkoxyalkyl, or aryloxy.

Additionally, the present invention provides for nonmutagenic, highly twisted colorants represented by the following structures

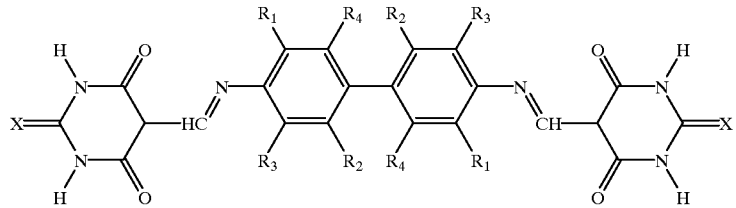

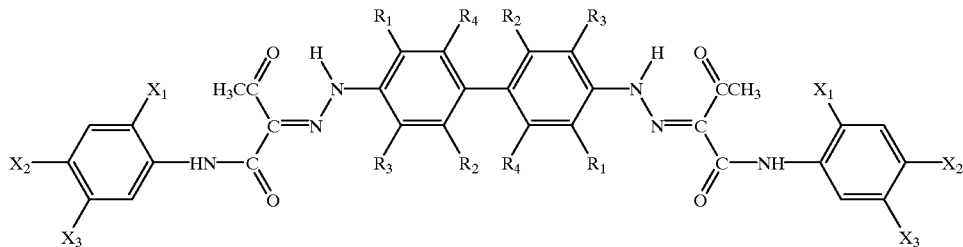

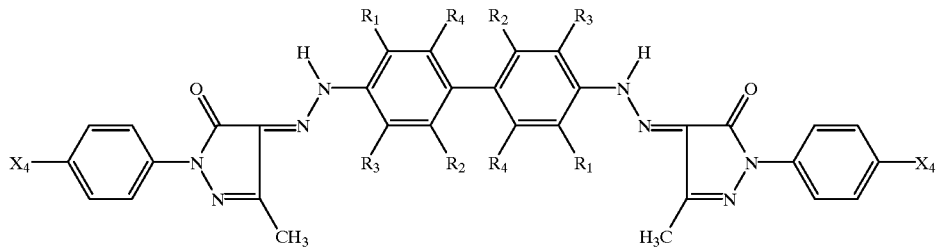

-continued

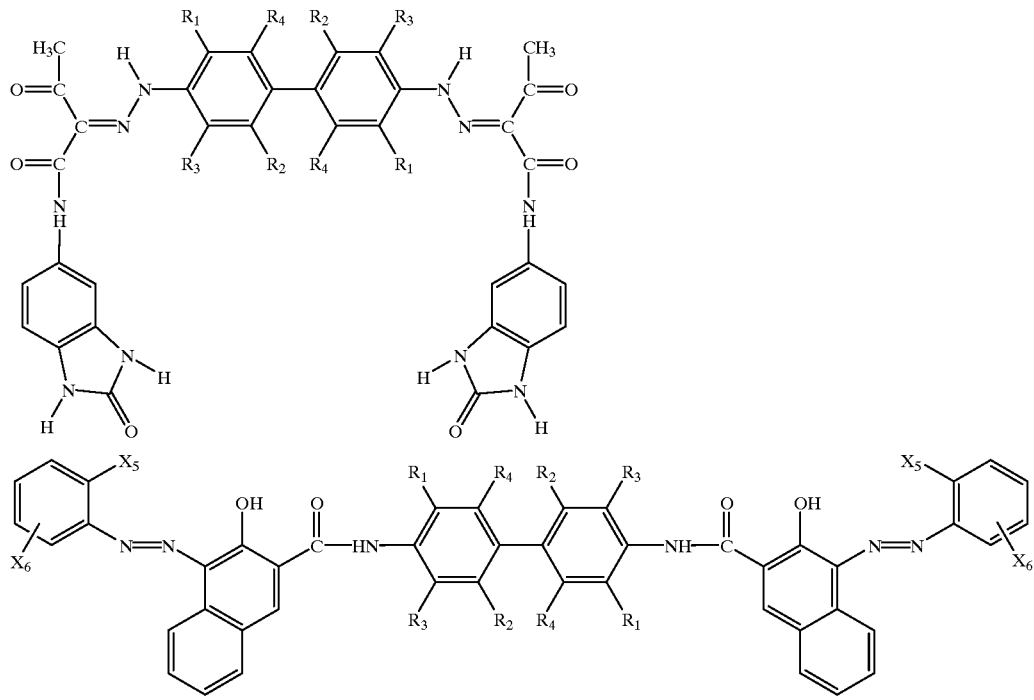

wherein each $R_1$ is the same and represents $C_{3-6}$-alkyl, $C_{3-6}$-alkoxy, $C_{3-6}$-hydroxyalkyl, $C_{3-6}$-alkoxyalkyl, or aryloxy, and each $R_2$ is the same and represents halogen, $C_{1-4}$-alkyl, $C_{1-4}$-alkoxy, $C_{1-4}$-hydroxyalkyl, $C_{1-4}$-alkoxyalkyl, or aryloxy, and each $R_3$ is the same and represents H or $CH_3$, and each $R_4$ is the same and represents H, halogen, $C_{1-4}$-alkyl, $C_{1-4}$-alkoxy, $C_{1-4}$-hydroxyalkyl, $C_{1-4}$-alkoxyalkyl, or aryloxy, and each X is the same and represents O, S, or NH, and each $X_1$ is the same and represents H, $CH_3$, $OCH_3$, or halogen, and each $X_2$ is the same and represents H, $OCH_3$, or halogen, and each $X_3$ is the same and represents H or halogen, and each $X_4$ is the same and represents H or halogen, and each $X_5$ is the same and represents H or halogen, and each $X_6$ is the same and represents H or halogen.

Hence, two objects of the present invention address simultaneously two important issues pertaining to the chemistry of the class of compounds commonly referred to as benzidines.

One object is that the nonmutagenic characteristic allows for a decrease in the occupational risk and environmental concern associated with the prior art benzidine-type compounds which has severely limited the scope of the commercialization of these substances, particularly in the last two decades because the genotoxicity of the prior art benzidine, analogues of benzidine, and certain dyes and pigments prepared therefrom, has resulted in legislation in many parts of the world either banning or severely limiting their production on a commercial scale.

The other object is that the inventive pigments are more hypsochromic since, due to the nature of the Π orbital interaction across the biphenyl linkage of benzidine-type compounds, the pigments prepared from the prior art benzidine-type compounds can exhibit wavelengths of maximum absorption more bathochromic than desired.

Some of the objects of the invention having been stated above, other objects will become evident as the description proceeds, when taken in connection with the accompanying Laboratory Examples as best described below.

DETAILED DESCRIPTION OF THE INVENTION

The present invention involves the incorporation of bulky substituents in a position ortho to each of the two amino functional groups, as well as bulky substituents in a position ortho to each side of the biphenyl linkage in the benzidine two-ring system to provide nonmutagenic, highly twisted benzidine derivatives and compounds made therefrom. The former incorporation provides for nonmutagenic benzidine-type compounds having lower occupational and environmental risk. The latter incorporation provides for benzidine-type compounds that are significantly rotated about the biphenyl linkage to reduce Π orbital overlap at this position and thereby to facilitate the preparation of pigments that are more hypsochromic relative to when, for example, hydrogen occupies that position ortho to each side of the biphenyl linkage.

Generally, the nonmutagenic, highly twisted benzidine derivatives and compounds made therefrom may be any alkyl-substituted, alkoxy-substituted, hydroxyalkyl-substituted, alkoxyalkyl-substituted, or aryloxy-substituted, or a mixture of alkyl, alkoxy, hydroxyalkyl, alkoxyalkyl, or aryloxy and di- or halogeno-substituted benzidine derivatives. In the twisted derivatives and compounds made therefrom, alkyl, alkoxy, hydroxyalkyl, alkoxyalkyl, (each with a minimum of three carbons), or aryloxy substituents are present ortho to each of the two amino functional groups, and also, alkyl, alkoxy, hydroxyalkyl, alkoxyalkyl, (each with a maximum of four carbons), or aryloxy, or halogeno substituents are present ortho to each side of the biphenyl linkage.

It is noted that by the term "highly twisted" as employed herein with respect to benzidine derivatives and compounds made therefrom, it is intended to mean benzidine derivatives and compounds made therefrom substituted both ortho to each of the two amino functional groups and ortho to each side of the biphenyl linkage.

The selective incorporation of four or more substituents, with two or more onto each of the rings of the benzidine two-ring system provides novel, highly twisted benzidine-type compounds that are not only occupationally and environmentally less harmful (i.e., nonmutagenic), but also that are more hypsochromic than many existing, commercialized benzidine-type compounds.

More specifically, in the preferred embodiment, the present invention provides for highly twisted, nonmutagenic benzidine derivatives of the following formula

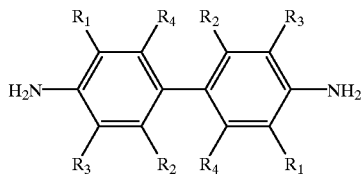

and which are useful as intermediates for the preparation of organic pigments, wherein each $R_1$ is the same and represents $C_{3-6}$-alkyl, $C_{3-6}$-alkoxy, $C_{3-6}$-hydroxyalkyl, $C_{3-6}$-alkoxyalkyl, or aryloxy, and each $R_2$ is the same and represents halogen, $C_{1-4}$-alkyl, $C_{1-4}$-alkoxy, $C_{1-4}$-hydroxyalkyl, $C_{1-4}$-alkoxyalkyl, or aryloxy, and each $R_3$ is the same and represents H or $CH_3$, and each $R_4$ is the same and represents H, halogen, $C_{1-4}$-alkyl, $C_{1-4}$-alkoxy, $C_{1-4}$-hydroxyalkyl, $C_{1-4}$-alkoxyalkyl, or aryloxy.

In the preferred embodiment, the above derivatives of benzidine are nonmutagenic in the Ames test. Conversely, common benzidines, for example, 3,3'-dichlorobenzidine, o-dianisidine and o-tolidine, are mutagenic in the Ames test and are regarded as cancer-suspect agents, and are therefore occupationally and environmentally hazardous.

It has been found that the preferred derivatives of benzidine are easily prepared and purified, and are ideally suited for use as intermediates in the preparation of organic pigments in which hypsochromic shifts are required relative to pigments derived from similarly substituted benzidine derivatives but having hydrogens in all four of positions $R_2$ and $R_4$. Furthermore, due to the ease with which the preferred derivatives of benzidine can be prepared and purified, these compounds are also logical candidates for use as intermediates in the synthesis of soluble organic dyes and in polymer synthesis.

In general, the novel, highly twisted derivatives of benzidine described above can be prepared and purified in good yields by a two stage procedure. First, the hydrazo intermediate can be prepared by reduction of a suitable nitrobenzene derivative, using, for example, a reducing metal and alkali in either an aqueous or organic medium. Preferably, the reduction is undertaken using zinc and sodium hydroxide in an organic medium such as ligroine. Second, a benzidine rearrangement of the hydrazo product can be undertaken using aqueous mineral acid solution.

In most cases, the precipitated crude acid salt product, e.g., dihydrochloride product, can be used directly for the preparation of organic pigments, following a simple purification procedure, such as washing with a solvent suitable for removal of impurities without dissolving the diamine salt, for instance, bisazomethine, disazoacetoacetanilide, disazopyrazolone, disazobenzimidazolone, and disazonaphthol pigments.

Thus, the present invention also provides for novel, highly twisted, nonmutagenic organic pigments of following formulae

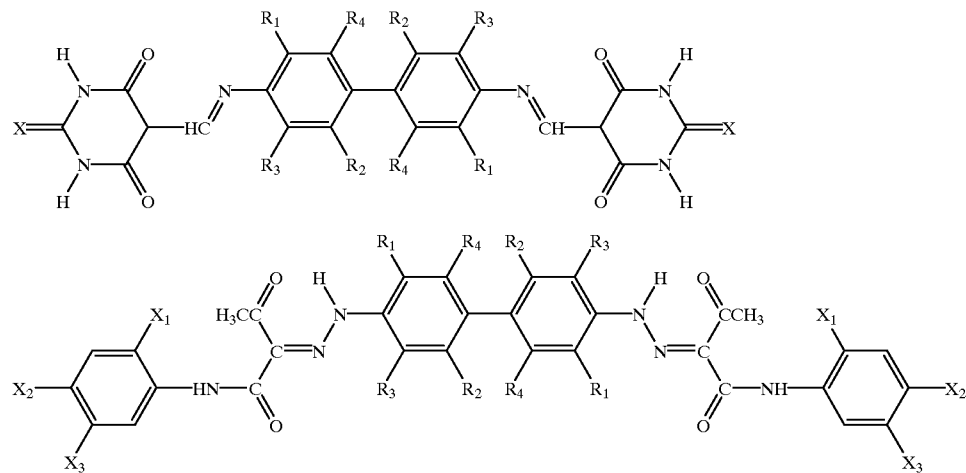

-continued

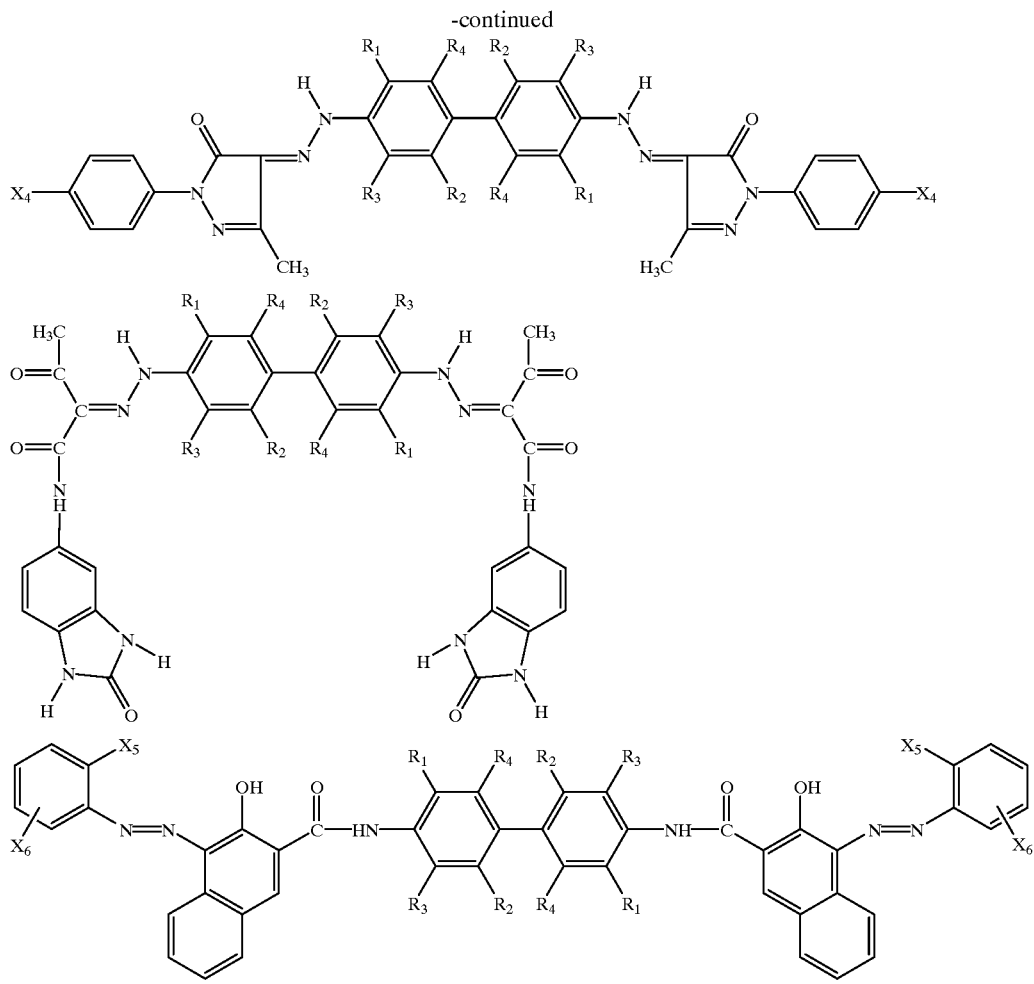

wherein
- each $R_1$ is the same and represents $C_{3-6}$-alkyl, $C_{3-6}$-alkoxy, $C_{3-6}$-hydroxyalkyl, $C_{3-6}$-alkoxyalkyl, or aryloxy, and
- each $R_2$ is the same and represents halogen, $C_{1-4}$-alkyl, $C_{1-4}$-alkoxy, $C_{1-4}$-hydroxyalkyl, $C_{1-4}$-alkoxyalkyl, or aryloxy, and
- each $R_3$ is the same and represents H or $CH_3$, and
- each $R_4$ is the same and represents H, halogen, $C_{1-4}$-alkyl, $C_{1-4}$-alkoxy, $C_{1-4}$-hydroxyalkyl, $C_{1-4}$-alkoxyalkyl, or aryloxy, and
- each X is the same and represents O, S, or NH, and
- each $X_1$ is the same and represents H, $CH_3$, $OCH_3$, or halogen, and
- each $X_2$ is the same and represents H, $OCH_3$, or halogen, and
- each $X_3$ is the same and represents H or halogen, and
- each $X_4$ is the same and represents H or halogen, and
- each $X_5$ is the same and represents H or halogen, and
- each $X_6$ is the same and represents H or halogen.

The above novel pigments are nonmutagenic in the Ames test and the Prival modification. As a result, the present invention, in the preferred embodiment, provides for pigments for which the preparation and use reduces the environmental risk as compared to the environmental risk accompanying the preparation and use of prior art colorants.

Also, the novel pigments, which are bright greenish-yellow, yellow, orange, red and brown in hue, (more particularly, greenish-yellow and yellow in hue) and which possess high tinctorial strength and high thermal stability, are suitable for use as pigments for inks (printing and writing), textiles, leather, paper, paints, etc.

Generally, the preparation of the nonmutagenic pigments varies depending on their chemical structure. For instance, in the case of bisazomethine pigments, an appropriate benzidine derivative is condensed with triethylorthoformate (abbreviated TEOF) and barbituric acid, or a derivative of the latter, in an organic solvent, such as N,N-dimethylformamide (abbreviated as DMF), at about 120° C., to form the nonmutagenic pigment, which is isolated by filtration, washed and dried. On the other hand, the synthesis of diarylide, disazopyrazolone, and disazobenzimidazolone pigments involves the tetrazotization of an appropriate benzidine derivative, followed by coupling with acetoacetanilide, 1-phenyl-3-methyl-5-pyrazolone, or 5-acetoacetylaminobenzimidazolone, respectively, at 0–20° C., to form the nonmutagenic pigments, which are isolated by filtration, washed and dried. Additionally, the synthesis of disazonaphthol pigments (referred to as condensed pigments) involves four steps. Aniline-compounds are diazotized and coupled with 3-hydroxy-2-naphthoic acid. The obtained diazo colorants are treated in chlorobenzene with $SOCl_2$ at 40–70° C. and the resulting monoazo acid chlorides are condensed with an appropriate benzidine derivative in chlorobenzene at the boiling point to form nonmutagenic pigments, which are isolated by filtration, washed and dried.

More particularly, the present invention provides for the preparation of novel highly twisted, nonmutagenic benzidine-type compounds suitable for use as intermediates in the preparation of organic pigments. The novel benzidine derivatives are potential replacements for the prior art common benzidines, that are known to be mutagenic in vitro and cancer-suspect agents. Also, the novel benzidine derivatives are particularly useful for the preparation of organic pigments for which hypsochromic shifts are desired relative to when common benzidines are employed.

Specific examples of suitable highly twisted derivatives of benzidine, which are nonmutagenic in the Ames test, are as follows

| Compound number | $R_1$ | $R_4$ | $R_3$ | $R_2$ |
|---|---|---|---|---|
| 7 | n-$(CH_2)_2CH_3$ | H | H | $CH_3$ |
| 8 | n-$(CH_2)_3CH_3$ | H | H | $CH_3$ |
| 9 | $CH(CH_3)_2$ | H | H | $CH_3$ |
| 10 | $CH_2CH(CH_3)_2$ | H | H | $CH_3$ |
| 11 | $CH(CH_3)CH_2CH_3$ | H | H | $CH_3$ |
| 12 | n-$O(CH_2)_2CH_3$ | H | H | $CH_3$ |
| 13 | n-$O(CH_2)_3CH_3$ | H | H | $CH_3$ |
| 14 | $OCH(CH_3)_2$ | H | H | $CH_3$ |
| 15 | $OCH_2CH(CH_3)_2$ | H | H | $CH_3$ |
| 16 | $OCH(CH_3)CH_2CH_3$ | H | H | $CH_3$ |
| 17 | OPh | H | H | $CH_3$ |
| 18 | $OCH_2CH_2OH$ | H | H | $CH_3$ |
| 19 | $OCH_2CH_2OCH_3$ | H | H | $CH_3$ |
| 20 | $CH_3$ | H | $CH_3$ | $CH_3$ |
| 21 | n-$(CH_2)_2CH_3$ | H | H | $OCH_3$ |
| 22 | n-$(CH_2)_3CH_3$ | H | H | $OCH_3$ |
| 23 | $CH(CH_3)_2$ | H | H | $OCH_3$ |
| 24 | $CH_2CH(CH_3)_2$ | H | H | $OCH_3$ |
| 25 | $CH(CH_3)CH_2CH_3$ | H | H | $OCH_3$ |
| 26 | n-$O(CH_2)_2CH_3$ | H | H | $OCH_3$ |
| 27 | n-$O(CH_2)_3CH_3$ | H | H | $OCH_3$ |
| 28 | $OCH(CH_3)_2$ | H | H | $OCH_3$ |
| 29 | $OCH_2CH(CH_3)_2$ | H | H | $OCH_3$ |
| 30 | $OCH(CH_3)CH_2CH_3$ | H | H | $OCH_3$ |
| 31 | OPh | H | H | $OCH_3$ |
| 32 | $OCH_2CH_2OH$ | H | H | $OCH_3$ |
| 33 | $OCH_2CH_2OCH_3$ | H | H | $OCH_3$ |
| 34 | $CH_3$ | $CH_3$ | H | $OCH_3$ |
| 35 | n-$(CH_2)_2CH_3$ | H | H | Cl |
| 36 | n-$(CH_2)_3CH_3$ | H | H | Cl |
| 37 | $CH(CH_3)_2$ | H | H | Cl |
| 38 | $CH_2CH(CH_3)_2$ | H | H | Cl |
| 39 | $CH(CH_3)CH_2CH_3$ | H | H | Cl |
| 40 | n-$O(CH_2)_2CH_3$ | H | H | Cl |
| 41 | n-$O(CH_2)_3CH_3$ | H | H | Cl |
| 42 | $OCH(CH_3)_2$ | H | H | Cl |
| 43 | $OCH_2CH(CH_3)_2$ | H | H | Cl |
| 44 | $OCH(CH_3)CH_2CH_3$ | H | H | Cl |
| 45 | OPh | H | H | Cl |
| 46 | $OCH_2CH_2OH$ | H | H | Cl |
| 47 | $OCH_2CH_2OCH_3$ | H | H | Cl |
| 48 | $CH_3$ | H | $CH_3$ | Cl |
| 49 | n-$(CH_2)_2CH_3$ | $CH_3$ | H | H |
| 50 | n-$(CH_2)_3CH_3$ | $CH_3$ | H | H |
| 51 | $CH(CH_3)_2$ | $CH_3$ | H | H |
| 52 | $CH_2CH(CH_3)_2$ | $CH_3$ | H | H |
| 53 | $CH(CH_3)CH_2CH_3$ | $CH_3$ | H | H |
| 54 | n-$O(CH_2)_2CH_3$ | $CH_3$ | H | H |

-continued

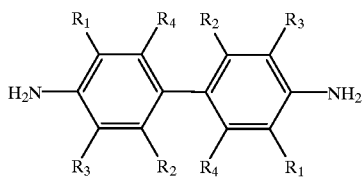

| Compound number | $R_1$ | $R_4$ | $R_3$ | $R_2$ |
|---|---|---|---|---|
| 55 | n-$O(CH_2)_3CH_3$ | $CH_3$ | H | H |
| 56 | $OCH(CH_3)_2$ | $CH_3$ | H | H |
| 57 | $OCH_2CH(CH_3)_2$ | $CH_3$ | H | H |
| 58 | $OCH(CH_3)CH_2CH_3$ | $CH_3$ | H | H |
| 59 | OPh | $CH_3$ | H | H |
| 60 | $OCH_2CH_2OH$ | $CH_3$ | H | H |
| 61 | $OCH_2CH_2OCH_3$ | $CH_3$ | H | H |
| 62 | $CH_3$ | $CH_3$ | $CH_3$ | H |
| 63 | n-$(CH_2)_2CH_3$ | $OCH_3$ | H | H |
| 64 | n-$(CH_2)_3CH_3$ | $OCH_3$ | H | H |
| 65 | $CH(CH_3)_2$ | $OCH_3$ | H | H |
| 66 | $CH_2CH(CH_3)_2$ | $OCH_3$ | H | H |
| 67 | $CH(CH_3)CH_2CH_3$ | $OCH_3$ | H | H |
| 68 | n-$O(CH_2)_2CH_3$ | $OCH_3$ | H | H |
| 69 | n-$O(CH_2)_3CH_3$ | $OCH_3$ | H | H |
| 70 | $OCH(CH_3)_2$ | $OCH_3$ | H | H |
| 71 | $OCH_2CH(CH_3)_2$ | $OCH_3$ | H | H |
| 72 | $OCH(CH_3)CH_2CH_3$ | $OCH_3$ | H | H |
| 73 | OPh | $OCH_3$ | H | H |
| 74 | $OCH_2CH_2OH$ | $OCH_3$ | H | H |
| 75 | $OCH_2CH_2OCH_3$ | $OCH_3$ | H | H |
| 76 | $CH_3$ | $OCH_3$ | $CH_3$ | H |
| 77 | n-$(CH_2)_2CH_3$ | Cl | H | H |
| 78 | n-$(CH_2)_3CH_3$ | Cl | H | H |
| 79 | $CH(CH_3)_2$ | Cl | H | H |
| 80 | $CH_2CH(CH_3)_2$ | Cl | H | H |
| 81 | $CH(CH_3)CH_2CH_3$ | Cl | H | H |
| 82 | n-$O(CH_2)_2CH_3$ | Cl | H | H |
| 83 | n-$O(CH_2)_3CH_3$ | Cl | H | H |
| 84 | $OCH(CH_3)_2$ | Cl | H | H |
| 85 | $OCH_2CH(CH_3)_2$ | Cl | H | H |
| 86 | $OCH(CH_3)CH_2CH_3$ | Cl | H | H |
| 87 | OPh | Cl | H | H |
| 88 | $OCH_2CH_2OH$ | Cl | H | H |
| 89 | $OCH_2CH_2OCH_3$ | Cl | H | H |
| 90 | $CH_3$ | Cl | $CH_3$ | H |

The key step in all commercial benzidine-type syntheses is the rearrangement of the intermediate hydrazo compound to the corresponding benzidine. This is usually effected using an aqueous mineral acid such as hydrochloric acid or sulfuric acid. The mechanism for the formation of the benzidine structure from nitrobenzenes has been widely studied, and the following major intermediates (for example, where R=H, Cl, Me, or OMe) are known to form

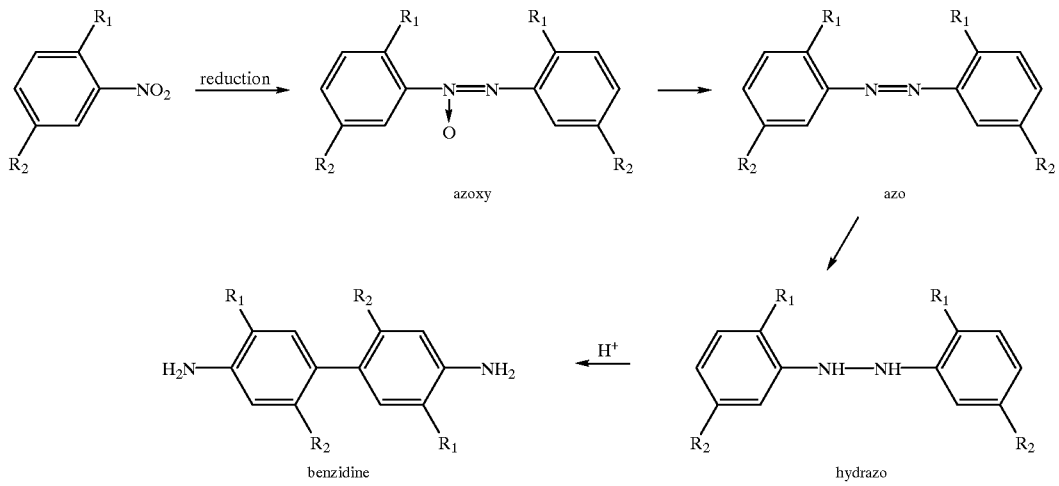

Therefore, in the present invention, the method of preparation of the nonmutagenic, highly twisted, benzidine derivatives comprises (1) formation of the tetra- or poly-substituted hydrazobenzene intermediate by alkaline reduction of a suitable di- or tri-substituted nitrobenzene, and (2) rearrangement of the hydrazobenzene intermediate using aqueous mineral acid.

In the first stage of the method, reduction of a suitable derivative of nitrobenzene can be effected in a number of ways, including utilization of an alkaline medium with zinc or sodium amalgams, zinc metal, or iron. The reduction method employed in the present invention utilized zinc dust and sodium hydroxide in an organic solvent chosen from either ortho-dichlorobenzene, ligroine (boiling range 90–110° C.), or ethanol.

An azobenzene derivative was gradually formed when a reaction vessel charged with a solution of an alkyl or alkoxy substituted nitrobenzene in, for example, ligroine and zinc was stirred at 70–80° C. and aqueous sodium hydroxide was added dropwise over several hours. The formation of the azo intermediate was readily apparent due to the development of a red-orange mixture.

The reduction can then progress further to the hydrazo intermediate, but commonly required the addition of more zinc, sodium hydroxide and also a small amount of water. The formation of the hydrazo intermediate can be observed by utilization of common techniques such as thin layer chromatography (TLC), but it is also indicated by decoloration of the reaction mixture. Once the reaction mixture became colorless, the formation of the hydrazo intermediate was complete and the second stage of the reaction, the benzidine rearrangement, was undertaken.

Following filtration of the reaction mixture, the organic layer containing the requisite hydrazobenzene intermediate was washed with dilute mineral acid, typically hydrochloric acid. This facilitated removal of substituted anilino by-product produced during the reduction of the substituted nitrobenzene.

For the second stage of the method, the hydrazobenzene was then treated with aqueous mineral acid, typically 10–40% (weight/weight) aqueous hydrochloric acid at 10–40° C., and the highly twisted, nonmutagenic benzidine dihydrochloride salt that precipitated was collected by filtration and purified by standard methods. Standard methods were used to convert the acid salt to the free base.

The structure and purity of the novel derivatives of benzidine were confirmed by proton nuclear magnetic resonance spectroscopy ($^1$H NMR), electron impact mass spectrometry (EI MS), and by combustion analysis.

Also, the present invention provides for novel organic pigments (synthesized as described herein) including, but not limited to, bisazomethines, disazoacetoacetanilides (diarylides), disazopyrazolones, disazobenzimidazolones, and disazonaphthols (condensed pigments). More preferably, the organic pigment is selected from the following structures, where each of $R_3$ and $R_4$ is H, Bisazomethines (bright yellow)

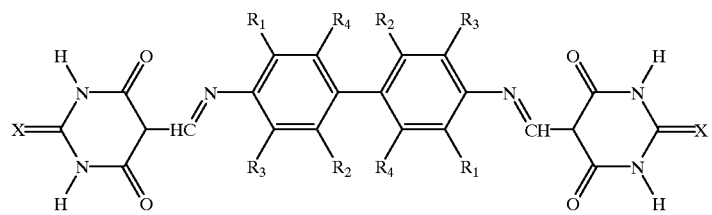

| Pigment number | $R_1$ | $R_2$ | X |
|---|---|---|---|
| 91 | OCH$_2$CH$_2$CH$_3$ | CH$_3$ | O |
| 92 | OCH$_2$CH$_2$CH$_3$ | OCH$_3$ | O |

-continued

| Pigment number | R₁ | R₂ | X |
|---|---|---|---|
| 93 | OCH₂CH₂CH₃ | CH₃ | S |
| 94 | OCH₂CH₂CH₃ | OCH₃ | S |

Diszoacetoacetanilides (yellow to orange)

| Pigment number | R₁ | R₂ | X₁ | X₂ | X₃ |
|---|---|---|---|---|---|
| 95 | OCH₂CH₂CH₃ | CH₃ | H | H | H |
| 96 | OCH₂CH₂CH₃ | OCH₃ | H | H | H |
| 97 | OCH₂CH₂CH₃ | CH₃ | OCH₃ | H | H |
| 98 | OCH₂CH₂CH₃ | OCH₃ | OCH₃ | H | H |
| 99 | OCH₂CH₂CH₃ | CH₃ | H | OCH₃ | H |
| 100 | OCH₂CH₂CH₃ | OCH₃ | H | OCH₃ | H |
| 101 | OCH₂CH₂CH₃ | CH₃ | CH₃ | H | H |
| 102 | OCH₂CH₂CH₃ | OCH₃ | CH₃ | H | H |
| 103 | OCH₂CH₂CH₃ | CH₃ | H | Cl | H |
| 104 | OCH₂CH₂CH₃ | OCH₃ | H | Cl | H |
| 105 | OCH₂CH₂CH₃ | CH₃ | Cl | H | Cl |
| 106 | OCH₂CH₂CH₃ | OCH₃ | Cl | H | Cl |
| 107 | OCH₂CH₂CH₃ | Cl | OCH₃ | H | H |

Disazopyrazolones (orange to reddish-orange)

| Pigment number | R₁ | R₂ | X₄ |
|---|---|---|---|
| 108 | OCH₂CH₂CH₃ | CH₃ | H |
| 109 | OCH₂CH₂CH₃ | OCH₃ | H |
| 110 | OCH₂CH₂CH₃ | CH₃ | Cl |
| 111 | OCH₂CH₂CH₃ | OCH₃ | Cl |
| 112 | OCH₂CH₂CH₃ | Cl | H |

Disazobenzimidazolones (yellow to orange)

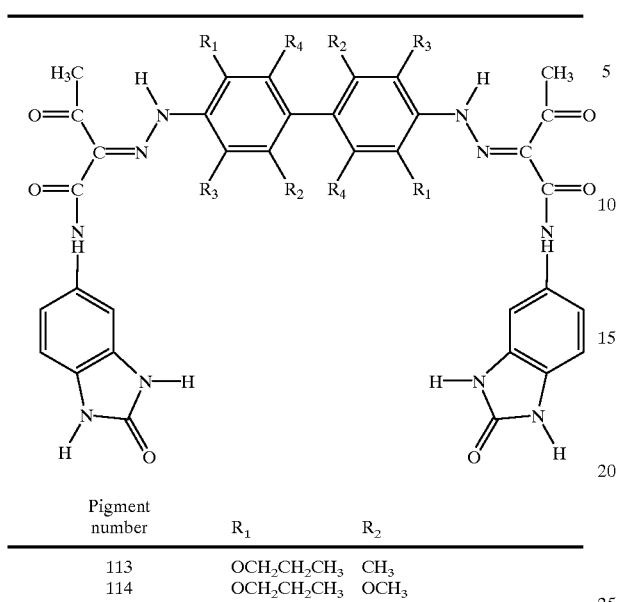

| Pigment number | $R_1$ | $R_2$ |
|---|---|---|
| 113 | $OCH_2CH_2CH_3$ | $CH_3$ |
| 114 | $OCH_2CH_2CH_3$ | $OCH_3$ |

Disazonaphthols (red to brown)

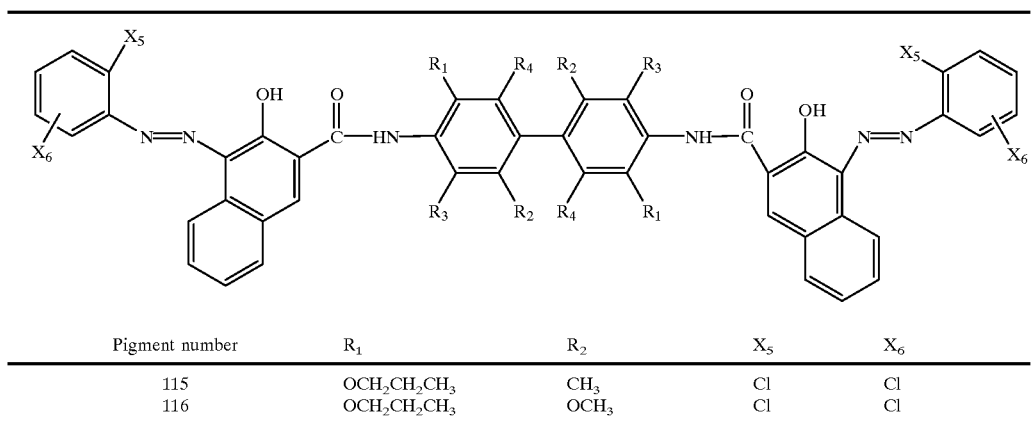

| Pigment number | $R_1$ | $R_2$ | $X_5$ | $X_6$ |
|---|---|---|---|---|
| 115 | $OCH_2CH_2CH_3$ | $CH_3$ | Cl | Cl |
| 116 | $OCH_2CH_2CH_3$ | $OCH_3$ | Cl | Cl |

Typically, in the case of bisazomethine pigments, the respective nonmutagenic benzidine derivative was dissolved in DMF, and at room temperature TEOF was added, followed by barbituric acid, or a derivative thereof, such as iminobarbituric acid or thiobarbituric acid. The reaction mixture was then heated gradually to 120° C. and maintained at this temperature until the reaction was complete. Upon completion of pigment formation, the reaction mixture was allowed to cool and then was filtered. The collected solid was washed, typically with hot methanol and hot water, and dried.

The diarylide, disazopyrazolone and disazobenzimidazolone pigments were synthesized by tetrazotization of nonmutagenic benzidines with $NaNO_2$ in the presence of HCl, followed by coupling of the resulting tetrazonium salt with acetoacetanilide, 1-phenyl-3-methyl-5-pyrazolone, or 5-acetoacetyloaminobenzimidazolone, respectively. Typically, the respective benzidine hydrochloride or free base was dispersed in an ice/water mixture in the presence of HCl. The mixture was stirred at 0–5° C. and sodium nitrite solution was added at such a rate to maintain a slight excess of $HNO_2$. The tetrazotization was continued for 30 minutes and the resulting tetrazonium salt was added dropwise at 0–20° C. to the coupling component dispersion, obtained by its dissolution in a $H_2O/NaOH$ mixture, followed by precipitation with $CH_3COOH/CH_3COONa$ (alternatively, with addition of surfactants) at pH=6, at such a rate that no presence of tetrazo intermediate was observed. The coupling was continued for several hours, and after the reaction was completed, the reaction mixture was heated to boiling. The obtained pigments were filtered hot, washed with hot water and dried.

Disazonaphthol pigments were synthesized via condensation of the appropriate benzidine with a monoazo acid/chloride, obtained by the coupling reaction of diazotized aniline compound with 3-hydroxy-2-naphthoic acid and its chlorination with $SOCl_2$. Typically, the azo dye was obtained by diazotization of aniline compound with $NaNO_2$ in the presence of HCl, followed by coupling with 3-hydroxy-2-naphthoic acid in the alkaline medium at 0–5° C. The azo dye was isolated by acidification with HCl, washed with water and dried. Dry azo dye was suspended in dry chlorobenzene and heated to 40° C. Next DMF and $SOCl_2$ were added at this temperature and the reaction mixture was stirred for 1 hour. After that time, additional $SOCl_2$ was added; the temperature was raised to 70° C. to complete the chlorination step. The acid chloride was isolated by filtration, washed with chlorobenzene and used for condensation with the nonmutagenic benzidine derivative. The condensation was carried out at the boil in chlorobenzene, and the pigment was isolated by filtration, washed with chlorobenzene and dried.

The structure and purity of each of the various pigments was confirmed by field desorption mass spectroscopy (FDMS), $^1$H-NMR spectroscopy (when possible) and combustion analysis.

Mutagenicity testing of the pure derivatives of benzidine was performed using the standard Ames test, as described by Ames et al. (Mutat. Res., 31 (1975) 347). Mutagenicity testing of the various pigments was performed using the standard Ames test, and also using the Prival modification, as described by Prival et al. (Mutat. Res., 97 (2) (1982) 103).

More particularly, two Salmonella typhimurium strains, TA98 and TA100, were employed for mutagenicity testing. All benzidine derivatives and the pigments made therefrom were evaluated in the presence and absence of metabolic activation. In the Ames test, metabolic activation was achieved using rat liver S9, whereas hamster liver S9 was employed in the Prival modification. A mutagenic response was recorded for a test compound if the number of revertant colonies counted was more than twice the number of spontaneous revertant colonies formed in the absence of the test compound. A nonmutagenic response (Ames negative or Prival negative) was recorded when the number of revertant colonies counted was less than twice the number of spontaneous revertant colonies. All of the tests for the benzidine derivatives and the pigments made therefrom were found to be nonmutagenic as reported in the Laboratory Examples below.

LABORATORY EXAMPLES

Twisted Benzidine Derivatives

To illustrate how nonmutagenic, highly twisted derivatives of benzidine can be prepared in accordance with the present invention, the following Examples set forth methods by which such compounds were produced.

Example 1

Preparation of 2,2'-dimethyl-5,5'-dipropoxybenzidine (compound 12)

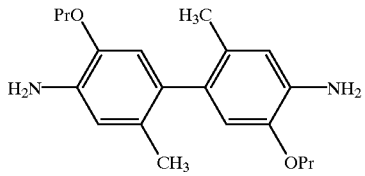

A solution of 4-methyl-2-nitropropoxybenzene (100.0 g) in ligroine (100 ml; boiling range 90–110° C.) was prepared and stirred at 25° C. To this yellow solution was charged zinc dust (110.6 g). The mixture was stirred and heated to between 70 and 80° C., and 50% aqueous sodium hydroxide solution (7.4 g) was added dropwise at 70–80° C.

Water (6.5 g) was then added at 70–80° C. The mixture gradually turned from yellow to orange to red.

After several hours, more zinc was charged (20.0 g) and the mixture was stirred until the organic layer turned colorless. Thin layer chromatography (TLC) was employed to follow the course of the reaction.

When the reaction was complete, the mixture was diluted by the portion-wise addition of ligroine (500 ml; boiling range 90–110° C.), filtered, and the filtrate allowed to cool. The organic layer was then washed with aqueous hydrochloric acid solution and then with distilled water.

The benzidine rearrangement was effected by the dropwise addition of 15% (w/w) aqueous hydrochloric acid (187 g) to the stirred organic layer at 20–25° C., and the precipitate was removed by filtration. The crude 2,2'-dimethyl-5,5-dipropoxybenzidine dihydrochloride was repeatedly slurried with acetone and filtered. The crude product was recrystallized from methanol/ethyl acetate. A product yield of 63% was recorded.

For structure confirmation, a portion of the dihydrochloride was converted to the free base. The structure of the free base was confirmed by $^1$H NMR, EI MS, and combustion analysis (Theory: C: 73.14, H: 8.59, N: 8.53. Found: C: 73.29, H: 8.65, N: 8.48). Melting point (uncorrected) of the free base was 136° C. Recrystallization of the dihydrochloride salt was not essential to obtain pure free base. The free base was found to be Ames negative.

Example 2

Preparation of 2,2'-dimethoxy-5,5'-dipropoxybenzidine (compound 26)

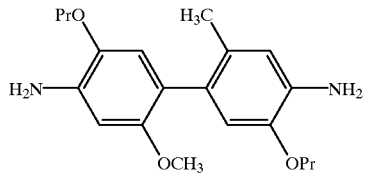

A solution of 4-methoxy-2-nitropropoxybenzene (100.0 g) in ligroine (100 ml) (boiling range 90–110° C.) was prepared and stirred at 25° C. To this yellow solution was charged zinc dust (93.0 g). The mixture was stirred and heated to between 70 and 80° C., and 50% aqueous sodium hydroxide solution (6.8 g) was added dropwise at 70–80° C. Water (6.0 g) was then added dropwise at 70–80° C. The mixture gradually turned from yellow to orange to red.

After several hours, more zinc was charged (18.6 g) and the mixture was stirred until the organic layer turned colorless. Thin layer chromatography (TLC) was employed to follow the course of the reaction.

When the reaction was complete, the mixture was diluted by the portion-wise addition of ligroine (500 ml; boiling range 90–110° C.), filtered, and the filtrate allowed to cool. The organic layer was then washed with aqueous hydrochloric acid solution and then with distilled water.

The benzidine rearrangement was effected by the dropwise addition of 15% (w/w) aqueous hydrochloric acid (172 g) to the stirred organic layer at 20–25° C., and the precipitate was removed by filtration. The crude 2,2'-dimethoxy-5,5'-dipropoxybenzidine dihydrochloride was slurried with acetone and filtered. The crude product was recrystallized from methanol/ethyl acetate. A product yield of 53% was recorded.

For structure confirmation, a portion of the dihydrochloride was converted to the free base. The structure of the free base was confirmed by $^1$H NMR, EI MS, and combustion analysis (Theory: C: 66.64, H: 7.83, N: 7.77. Found: C: 66.74, H: 7.86, N: 7.83). Melting point (uncorrected) of the free base was 123° C. This product was found to be Ames negative.

Pigments from Twisted Benzidine Derivatives

To illustrate how bisazomethine, diarylide, disazopyrazolone, disazobenzimidazolone, and disazonaphthol pigments derived from nonmutagenic twisted derivatives of benzidine can be prepared in accordance with the present invention, the following Examples set forth methods by which such pigments were produced.

Example 3

Preparation of Pigment 93

Four grams of 2,2'-dimethyl-5,5'-dipropoxybenzidine (from Example 1) was dissolved in DMF (40 ml), followed by the addition of 4,6-dihydroxy-2-mercaptopyrimidine (3.87 g). Next, an additional amount of DMF (40 ml) was added and the reaction mixture was heated to 45° C. until complete solution was obtained.

After 30 minutes, TEOF (4.10 ml) was charged and the reaction mixture was stirred for several minutes at 25° C. At that point the reaction mixture was heated to 80° C., and after 1 hour the temperature was raised to 120° C. until the reaction was complete. The reaction mixture was allowed to cool to 80° C. and the pigment was isolated by filtration. The solid was stirred with boiling methanol and filtered again. Next, the colorant was washed with hot water and dried at 40° C.

A product yield of 95% was recorded. FDMS and combustion analysis confirmed the structure of the greenish-yellow colorant, which was negative in both the Ames test and the Prival modification.

Example 4

Preparation of Pigment 95

A suspension of 2,2'-dimethyl-5,5'-dipropoxybenzidine dihydrochloride (4.00 g) (from Example 1) in $H_2O$ (20 ml), HCl 36% (4 ml) and ice (4.80g) was prepared and stirred for several minutes. To this reaction mixture, at 0–5° C. temperature, $NaNO_2$ (1.38 g) dissolved in $H_2O$ (12 ml) was added dropwise at such a rate so as to maintain a slight excess of $HNO_2$. The tetrazotization was continued for 30 minutes, and then excess of $HNO_2$ was decomposed using sulfamic acid. The tetrazonium salt solution was additionally purified by activated carbon treatment and added dropwise at 0–5° C. at pH=6 under the surface of a suspension of acetoacetanilide (3.70 g), obtained by its dissolution in $H_2O$ (100 ml) containing NaOH (0.64 g), followed by precipitation with HOAc (1.60 ml) and $NaOAc.3H_2O$ (8.64 g), at such a rate that no presence of tetrazo-intermediate was observed. The coupling reaction was continued for several hours and next the reaction mixture was heated to the boil. The pigment was filtered hot, boiled several times with hot water, filtered again, and dried at 40° C.

A product yield of 89% was recorded. FDMS, $^1$H-NMR and combustion analysis confirmed the structure of the bright yellow pigment, which was negative in both the Ames test and the Prival modification.

Example 5

Preparation of Pigment 108

The tetrazonium component was prepared by the method described in Example 4 and added dropwise at 0–5° C., at pH=6 to a suspension of 1-phenyl-3-methyl-5-pyrazolone (3.48 g) obtained by its dissolution in $H_2O$ (100 ml) with NaOH (0.64 g), followed by precipitation with HOAc (1.60 ml) and $NaOAc.3H_2O$ (8.64 g). The coupling reaction was carried out in the way described in Example 4. The pigment was hot filtered, washed with hot water several times and dried in the oven at 40° C.

A product yield of 75% was recorded. FDMS, $^1$H-NMR and combustion analysis confirmed the structure of the bright orange pigment, which was negative in both the Ames test and the Prival modification.

Example 6

Preparation of Pigment 113

The tetrazonium component was prepared in the way described in Example 4 and added dropwise at 20° C. at pH=6 to a suspension of 5-acetoacetylaminobenzimidazolone (4.90 g). This suspension was prepared in the way described in Example 4, followed by the addition of a small amount of Surfarynol and Triton X-100. The pigment was isolated in the way described in Example 4 and dried at 40° C. Then, dry pigment was boiled with DMF for several minutes. After cooling to 50° C., the pigment was collected by filtration, washed with water, and dried at 40° C.

A product yield of 85% was recorded. FDMS and combustion analysis confirmed the structure of the bright yellow pigment, which was negative in both the Ames test and the Prival modification.

Example 7

Preparation of Pigment 115

A mixture of 2,5-dichloroaniline (8.10 g) in $H_2O$ (50 ml) and 30% HCl (15 ml) was heated at 60° C. for several minutes. Next ice was added, and at 0–2° C. the reaction mixture was treated with $NaNO_2$ (3.45 g) dissolved in $H_2O$ (15 ml). The diazotization was continued for several minutes, followed by filtration of a small amount of solid. The diazonium salt was added dropwise to 3-hydroxy-2-naphthoic acid (10 g) dissolved in $H_2O$ (200 ml) containing 30% NaOH (5 ml) and $Na_2CO_3$ (17 g) at such a rate so as to maintain the temperature at 0–2° C. The coupling was continued until it was complete.

The monoazo dye was isolated by acidification with 30% HCl filtered, washed with water and dried at 40° C. The resulting monoazo dye was dispersed in dry chlorobenzene and heated to 40° C. To this mixture, DMF (0.5 ml) and $SOCl_2$ (2.5 ml) were added and the chlorination was continued for 1 hour. Then, additional $SOCl_2$ (2 ml) was added; the temperature was raised to 70° C.; and the reaction mixture was stirred for 2 hours. The resulting acid chloride was filtered and washed with chlorobenzene. Next, it was dispersed again in dry chlorobenzene and added to a solution of 2,2'-dimethyl-5,5'-dipropoxybenzidine (6.68 g) in chlorobenzene at 70° C. The reaction mixture was then heated to boiling and held there until the condensation was complete. The pigment was filtered hot, washed with chlorobenzene and dried at 40° C.

A product yield of 70% was recorded. FDMS and combustion analysis confirmed the structure of the bright red pigment, which was negative in both the Ames test and the Prival modification.

Example 8

Preparation of Pigment 98

A suspension of 2,2'-dimethoxy-5,5'-dipropoxybenzidine (4.00 g) in $H_2O$ (16 ml), HCl 36% (6 ml) and ice (4.80 g) was prepared and stirred for several minutes. To this reaction mixture, at 0–5° C., $NaNO_2$ (1.54 g) dissolved in $H_2O$ (16 ml) was added dropwise at a rate so as to maintain a slight excess of $HNO_2$. Tetrazotization was continued for several minutes, and excess $HNO_2$ was decomposed using sulfamic acid. The tetrazonium salt solution was additionally purified using activated carbon, and added dropwise at 0–5° C. and pH=6, under the surface of a suspension of acetoacetanilide (4.11 g), obtained by its dissolution in $H_2O$ containing NaOH (0.76 g), followed by precipitation with HOAc (1.91 ml) and $NaOAc.3H_2O$ (10.35 g) at which point the tetrazo intermediate was consumed. The coupling reaction was continued for several hours and then the reaction mixture was heated to the boil. The pigment was filtered hot, boiled several times in hot water, filtered hot again, and dried at 40° C.

A product yield of 58.5% was recorded. FDMS, $^1$H-NMR and combustion analysis confirmed the structure of the yellow-orange pigment, which was negative in both the Ames test and Prival modification.

Example 9

Preparation of Pigment 107

A suspension of 2,2'-dichloro-5,5'-dipropoxybenzidine dihydrochloride (4.00 g) in $H_2O$ (3.75 ml), HCl 36% (4.00 ml) and ice (4.80 g) was prepared and stirred for several minutes. To this reaction mixture, at 0–5° C., $NaNO_2$ (1.48 g) dissolved in $H_2O$ (12 ml) was added dropwise at a rate so as to maintain a slight excess of $HNO_2$.

Tetrazotization was continued for 30 minutes, and then excess $HNO_2$ was decomposed using sulfamic acid. The tetrazonium salt solution was additionally purified using activated carbon and added dropwise at 0–5° C. and pH=6, under the surface of suspension of o-acetoacetaniside (4.44 g), obtained by its dissolution in $H_2O$ containing NaOH (0.68 g), followed by precipitation from HOAc (1.60 ml) and $NaOAC.3H_2O$ (8.82 g) at which point the tetrazo intermediate was consumed. The coupling reaction was continued for several hours and then the reaction mixture was heated to the boil. The pigment was filtered hot, boiled several times in hot water, filtered hot again, and dried at 40° C.

A product yield of 62.5% was recorded. FDMS, $^1$H-NMR and combustion analysis confirmed the structure of the yellow pigment, which was negative in both the Ames test and the Prival modification.

It will be understood that various details of the present invention may be changed without departing from the spirit and scope of the invention. Furthermore, the foregoing examples are for illustrative purposes only, and in no way are intended to limit the scope of the invention as defined by the claims.

What is claimed is:

1. A nonmutagenic, highly twisted benzidine compound or acid salts thereof, wherein the benzidine compound or acid salts thereof have (1) two phenyl rings with a biphenyl linkage therebetween, and (2) a first and a second amino functional moiety with the first amino moiety on one phenyl ring para to the biphenyl linkage and the second amino moiety on the other phenyl ring para to the biphenyl linkage, and (3) at least four substituents on the two phenyl rings, wherein the substituents are selected from the group consisting of alkyl, alkoxy, hydroxyalkyl, alkoxyalkyl, aryloxy, and halogeno substituents, and mixtures thereof, with (A) one each of two of the same alkyl, alkoxy, hydroxyalkyl, alkoxyalkyl, and aryloxy substituents present ortho respectively to each of the two amino functional groups, provided that the alkyl, alkoxy, hydroxyalkyl, and alkoxyalkyl each has a minimum of three carbons, and (B) one each of two of the same alkyl, alkoxy, hydroxyalkyl, alkoxyalkyl, aryloxy, and halogeno substituents present ortho respectively to each side of the biphenyl linkage, provided that the alkyl, alkoxy, hydroxyalkyl, and alkoxyalkyl each has a maximum of four carbons, and wherein (A) and (B) are para to each other for each of the two pairs of (A) and (B).

2. The nonmutagenic, highly twisted compound or benzidine and acid salts thereof according to claim 1, wherein the benzidine compound has the formula

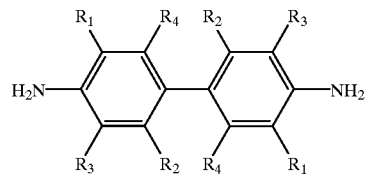

wherein each $R_1$ is the same and is a substituent selected from the group consisting of $C_{3-6}$-alkyl, $C_{3-6}$-alkoxy, $C_{3-6}$-hydroxyalkyl, $C_{3-6}$alkoxyalkyl, and aryloxy, and each $R_2$ is the same and is a substituent selected from the group consisting of halogen, $C_{1-4}$-alkyl, $C_{1-4}$-alkoxy, $C_{1-4}$-hydroxyalkyl, $C_{1-4}$-alkoxyalkyl, and aryloxy, and each $R_3$ is the same and is a substituent selected from the group consisting of H, and $CH_3$, and each $R_4$ is the same and is a substituent selected from the group consisting of H, halogen, $C_{1-4}$-alkyl, $C_{1-4}$-alkoxy, $C_{1-4}$-hydroxyalkyl, $C_{1-4}$-alkoxyalkyl, and aryloxy.

3. The benzidine compound or and acid salts thereof according to claim 2, wherein the benzidine compound is selected from the group consisting of compounds 7 through 90, where each of $R_1$, $R_2$, $R_3$, and $R_4$ is defined as follows:

| Compound number | $R_1$ | $R_4$ | $R_3$ | $R_2$ |
|---|---|---|---|---|
| 7 | n-$(CH_2)_2CH_3$ | H | H | $CH_3$ |
| 8 | n-$(CH_2)_3CH_3$ | H | H | $CH_3$ |
| 9 | $CH(CH_3)_2$ | H | H | $CH_3$ |
| 10 | $CH_2CH(CH_3)_2$ | H | H | $CH_3$ |
| 11 | $CH(CH_3)CH_2CH_3$ | H | H | $CH_3$ |
| 12 | n-$O(CH_2)_2CH_3$ | H | H | $CH_3$ |
| 13 | n-$O(CH_2)_3CH_3$ | H | H | $CH_3$ |
| 14 | $OCH(CH_3)_2$ | H | H | $CH_3$ |
| 15 | $OCH_2CH(CH_3)_2$ | H | H | $CH_3$ |
| 16 | $OCH(CH_3)CH_2CH_3$ | H | H | $CH_3$ |
| 17 | OPh | H | H | $CH_3$ |
| 18 | $OCH_2CH_2OH$ | H | H | $CH_3$ |
| 19 | $OCH_2CH_2OCH_3$ | H | H | $CH_3$ |
| 20 | $CH_3$ | H | $CH_3$ | $CH_3$ |
| 21 | n-$(CH_2)_2CH_3$ | H | H | $OCH_3$ |
| 22 | n-$(CH_2)_3CH_3$ | H | H | $OCH_3$ |
| 23 | $CH(CH_3)_2$ | H | H | $OCH_3$ |
| 24 | $CH_2CH(CH_3)_2$ | H | H | $OCH_3$ |
| 25 | $CH(CH_3)CH_2CH_3$ | H | H | $OCH_3$ |
| 26 | n-$O(CH_2)_2CH_3$ | H | H | $OCH_3$ |
| 27 | n-$O(CH_2)_3CH_3$ | H | H | $OCH_3$ |
| 28 | $OCH(CH_3)_2$ | H | H | $OCH_3$ |
| 29 | $OCH_2CH(CH_3)_2$ | H | H | $OCH_3$ |
| 30 | $OCH(CH_3)CH_2CH_3$ | H | H | $OCH_3$ |
| 31 | OPh | H | H | $OCH_3$ |
| 32 | $OCH_2CH_2OH$ | H | H | $OCH_3$ |
| 33 | $OCH_2CH_2OCH_3$ | H | H | $OCH_3$ |
| 34 | $CH_3$ | $CH_3$ | H | $OCH_3$ |
| 35 | n-$(CH_2)_2CH_3$ | H | H | Cl |
| 36 | n-$(CH_2)_3CH_3$ | H | H | Cl |
| 37 | $CH(CH_3)_2$ | H | H | Cl |
| 38 | $CH_2CH(CH_3)_2$ | H | H | Cl |
| 39 | $CH(CH_3)CH_2CH_3$ | H | H | Cl |
| 40 | n-$O(CH_2)_2CH_3$ | H | H | Cl |
| 41 | n-$O(CH_2)_3CH_3$ | H | H | Cl |
| 42 | $OCH(CH_3)_2$ | H | H | Cl |
| 43 | $OCH_2CH(CH_3)_2$ | H | H | Cl |
| 44 | $OCH(CH_3)CH_2CH_3$ | H | H | Cl |
| 45 | OPh | H | H | Cl |
| 46 | $OCH_2CH_2OH$ | H | H | Cl |
| 47 | $OCH_2CH_2OCH_3$ | H | H | Cl |
| 48 | $CH_3$ | H | $CH_3$ | Cl |
| 49 | n-$(CH_2)_2CH_3$ | $CH_3$ | H | H |

-continued

| Compound number | $R_1$ | $R_4$ | $R_3$ | $R_2$ |
|---|---|---|---|---|
| 50 | n-$(CH_2)_3CH_3$ | $CH_3$ | H | H |
| 51 | $CH(CH_3)_2$ | $CH_3$ | H | H |
| 52 | $CH_2CH(CH_3)_2$ | $CH_3$ | H | H |
| 53 | $CH(CH_3)CH_2CH_3$ | $CH_3$ | H | H |
| 54 | n-$O(CH_2)_2CH_3$ | $CH_3$ | H | H |
| 55 | n-$O(CH_2)_3CH_3$ | $CH_3$ | H | H |
| 56 | $OCH(CH_3)_2$ | $CH_3$ | H | H |
| 57 | $OCH_2CH(CH_3)_2$ | $CH_3$ | H | H |
| 58 | $OCH(CH_3)CH_2CH_3$ | $CH_3$ | H | H |
| 59 | OPh | $CH_3$ | H | H |
| 60 | $OCH_2CH_2OH$ | $CH_3$ | H | H |
| 61 | $OCH_2CH_2OCH_3$ | $CH_3$ | H | H |
| 62 | $CH_3$ | $CH_3$ | $CH_3$ | H |
| 63 | n-$(CH_2)_2CH_3$ | $OCH_3$ | H | H |
| 64 | n-$(CH_2)_3CH_3$ | $OCH_3$ | H | H |
| 65 | $CH(CH_3)_2$ | $OCH_3$ | H | H |
| 66 | $CH_2CH(CH_3)_2$ | $OCH_3$ | H | H |
| 67 | $CH(CH_3)CH_2CH_3$ | $OCH_3$ | H | H |
| 68 | n-$O(CH_2)_2CH_3$ | $OCH_3$ | H | H |
| 69 | n-$O(CH_2)_3CH_3$ | $OCH_3$ | H | H |
| 70 | $OCH(CH_3)_2$ | $OCH_3$ | H | H |
| 71 | $OCH_2CH(CH_3)_2$ | $OCH_3$ | H | H |
| 72 | $OCH(CH_3)CH_2CH_3$ | $OCH_3$ | H | H |
| 73 | OPh | $OCH_3$ | H | H |
| 74 | $OCH_2CH_2OH$ | $OCH_3$ | H | H |
| 75 | $OCH_2CH_2OCH_3$ | $OCH_3$ | H | H |
| 76 | $CH_3$ | $OCH_3$ | $CH_3$ | H |
| 77 | n-$(CH_2)_2CH_3$ | Cl | H | H |
| 78 | n-$(CH_2)_3CH_3$ | Cl | H | H |
| 79 | $CH(CH_3)_2$ | Cl | H | H |
| 80 | $CH_2CH(CH_3)_2$ | Cl | H | H |
| 81 | $CH(CH_3)CH_2CH_3$ | Cl | H | H |
| 82 | n-$O(CH_2)_2CH_3$ | Cl | H | H |
| 83 | n-$O(CH_2)_3CH_3$ | Cl | H | H |
| 84 | $OCH(CH_3)_2$ | Cl | H | H |
| 85 | $OCH_2CH(CH_3)_2$ | Cl | H | H |
| 86 | $OCH(CH_3)CH_2CH_3$ | Cl | H | H |
| 87 | OPh | Cl | H | H |
| 88 | $OCH_2CH_2OH$ | Cl | H | H |
| 89 | $OCH_2CH_2OCH_3$ | Cl | H | H |
| 90 | $CH_3$ | Cl | $CH_3$ | H | for each respective compound 7 through 90.

4. The benzidine compound or and acid salts thereof according to claim 3, wherein the benzidine compound is selected from the group consisting of 2,2'-dimethyl-5,5'-dipropoxybenzidine and 2,2'-dimethoxy-5,5'-dipropoxybenzidine.

5. The benzidine compound or and acid salts thereof according to claim 2, wherein the benzidine compound or and acid salts thereof are nonmutagenic in accordance with the Ames test.

6. A method of making a nonmutagenic, highly twisted benzidine compound or acid salts thereof, wherein the benzidine compound has the formula

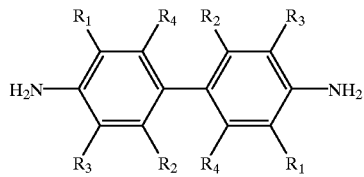

wherein
each $R_1$ is the same and is a substituent selected from the group consisting of $C_{3-6}$-alkyl, $C_{3-6}$-alkoxy, $C_{3-6}$-hydroxyalkyl, $C_{3-6}$-alkoxyalkyl, and aryloxy, and
each $R_2$ is the same and is a substituent selected from the group consisting of halogen, $C_{1-4}$-alkyl, $C_{1-4}$-alkoxy, $C_{1-4}$-hydroxyalkyl, $C_{1-4}$-alkoxyalkyl, and aryloxy, and each $R_3$ is the same and is a substituent selected from the group consisting of H and $CH_3$, and
each $R_4$ is the same and is a substituent selected from the group consisting of H, halogen, $C_{1-4}$-alkyl, $C_{1-4}$-alkoxy, $C_{1-4}$-hydroxyalkyl, $C_{1-4}$-alkoxyalkyl, and aryloxy, the method comprising (1) forming a correspondingly substituted hydrazobenzene intermediate by alkaline reduction of a suitably substituted nitrobenzene and (2) rearranging the resulting hydrazobenzene intermediate with acid.

7. A nonmutagenic pigment prepared from a nonmutagenic, highly twisted benzidine compound or acid salts thereof, wherein the benzidine compound or acid salts thereof have (1) two phenyl rings with a biphenyl linkage therebetween, (2) a first and a second amino functional moiety with the first amino moiety on one phenyl ring para to the biphenyl linkage and the second amino moiety on the other phenyl ring para to the second amino moiety on the other phenyl ring para to the biphenyl linkage, and (3) at least four substituents on the two phenyl rings, wherein the substituents are selected from the group consisting of alkyl, alkoxy, hydroxyalkyl, alkoxyalkyl, aryloxy, and halageno substituents, and mixtures thereof, with (A) one each of two of the same alkyl, alkoxy, hydroxyalkyl, alkoxyalkyl, and aryloxy substituents present ortho respectively to each of the two amino functional groups, provided that the alkyl, alkoxy, hydroxyalkyl, and alkoxyalkyl each has a minimum of three carbons, and (B) one each of two of the same alkyl, alkoxy, hydroxyalkyl, alkoxyalkyl, aryloxy, and halogeno substituents present ortho respectively to each side of the biphenyl linkage, provided that the alkyl, alkoxy, hydroxyalkyl, and alkoxyalkyl each has a maximum of four carbons, and wherein (A) and (B) are para to each other for each of the two pairs of (A) and (B).

8. The pigment according to claim 7, wherein the pigment is prepared from a nonmutagenic, highly twisted benzidine compound or acid salts thereof, wherein the benzidine compound has the formula

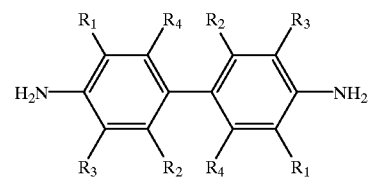

wherein
each $R_1$ is the same and is a substituent selected from the group consisting of $C_{3-6}$-alkyl, $C_{3-6}$-alkoxy, $C_{3-6}$-hydroxyalkyl, $C_{3-6}$-alkoxyalkyl, and aryloxy, and
each $R_2$ is the same and is a substituent selected from the group consisting of halogen, $C_{1-4}$-alkyl, $C_{1-4}$-alkoxy, $C_{1-4}$-hydroxyalkyl, $C_{1-4}$-alkoxyalkyl, and aryloxy, and
each $R_3$ is the same and is a substituent selected from the group consisting of H and $CH_3$, and
each $R_4$ is the same and is a substituent selected from the group consisting of H, halogen, $C_{1-4}$-alkyl, $C_{1-4}$-alkoxy, $C_{1-4}$-hydroxyalkyl, $C_{1-4}$-alkoxyalkyl, and aryloxy.

9. The pigment according to claim 8, wherein the pigment is selected from the group consisting of bisazomethines, disazoacetoacetanilides, disazopyrazolones, disazobenzimidazolones, and disazonaphthols.

10. The pigment according to claim 9, wherein the pigment is selected from the group consisting of pigments 91 through 116, where each of $R_3$ and $R_4$ is H, and each of $R_1$, $R_2$, X, $X_1$, $X_2$, $X_3$, $X_4$, $X_5$, and $X_6$ is defined as follows:

Bisazomethines (bright yellow)

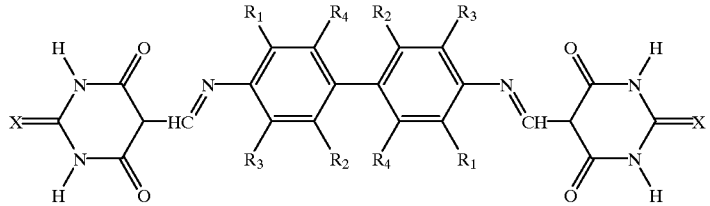

Bisazomethines (bright yellow)

| Pigment number | $R_1$ | $R_2$ | X |
|---|---|---|---|
| 91 | $OCH_2CH_2CH_3$ | $CH_3$ | O |
| 92 | $OCH_2CH_2CH_3$ | $OCH_3$ | O |
| 93 | $OCH_2CH_2CH_3$ | $CH_3$ | S |
| 94 | $OCH_2CH_2CH_3$ | $OCH_3$ | S |

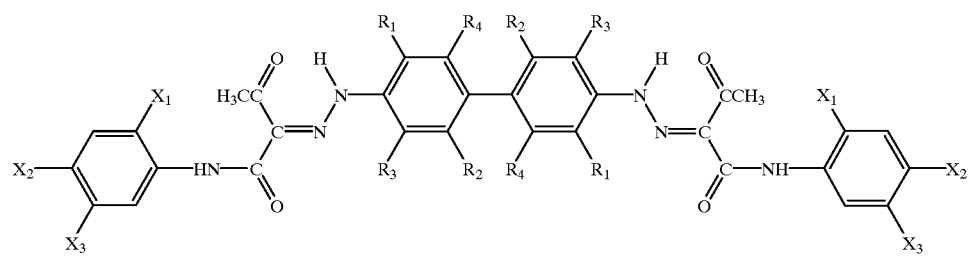

Disazoacetoacetanilides (yellow to orange)

| Pigment number | $R_1$ | $R_2$ | $X_1$ | $X_2$ | $X_3$ |
|---|---|---|---|---|---|
| 95 | $OCH_2CH_2CH_3$ | $CH_3$ | H | H | H |
| 96 | $OCH_2CH_2CH_3$ | $OCH_3$ | H | H | H |
| 97 | $OCH_2CH_2CH_3$ | $CH_3$ | $OCH_3$ | H | H |
| 98 | $OCH_2CH_2CH_3$ | $OCH_3$ | $OCH_3$ | H | H |
| 99 | $OCH_2CH_2CH_3$ | $CH_3$ | H | $OCH_3$ | H |
| 100 | $OCH_2CH_2CH_3$ | $OCH_3$ | H | $OCH_3$ | H |
| 101 | $OCH_2CH_2CH_3$ | $CH_3$ | $CH_3$ | H | H |
| 102 | $OCH_2CH_2CH_3$ | $OCH_3$ | $CH_3$ | H | H |
| 103 | $OCH_2CH_2CH_3$ | $CH_3$ | H | Cl | H |
| 104 | $OCH_2CH_2CH_3$ | $OCH_3$ | H | Cl | H |
| 105 | $OCH_2CH_2CH_3$ | $CH_3$ | Cl | H | Cl |
| 106 | $OCH_2CH_2CH_3$ | $OCH_3$ | Cl | H | Cl |
| 107 | $OCH_2CH_2CH_3$ | Cl | $OCH_3$ | H | H |

Disazopyrazolones (orange to reddish-orange)

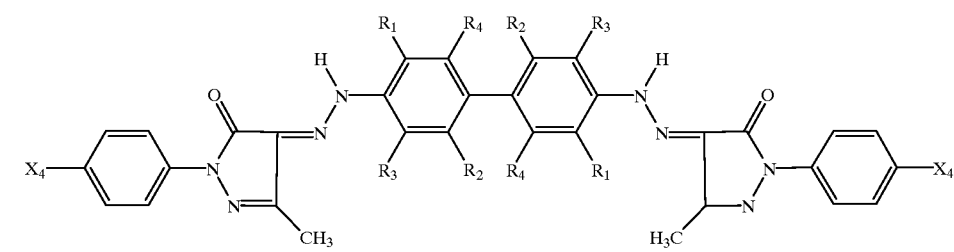

| Pigment number | $R_1$ | $R_2$ | $X_4$ |
|---|---|---|---|
| 108 | $OCH_2CH_2CH_3$ | $CH_3$ | H |
| 109 | $OCH_2CH_2CH_3$ | $OCH_3$ | H |
| 110 | $OCH_2CH_2CH_3$ | $CH_3$ | Cl |

-continued

| Pigment number | R₁ | R₂ | X₄ |
|---|---|---|---|
| 111 | OCH₂CH₂CH₃ | OCH₃ | Cl |
| 112 | OCH₂CH₂CH₃ | Cl | H |

Disazobenzimidazolones (yellow to orange)

Disazobenzimidazolones (yellow to orange)

| Pigment number | R₁ | R₂ |
|---|---|---|
| 113 | OCH₂CH₂CH₃ | CH₃ |
| 114 | OCH₂CH₂CH₃ | OCH₃ |

Disazonaphthols (red to brown)

| Pigment number | R₁ | R₂ | X₅ | X₆ |
|---|---|---|---|---|
| 115 | OCH₂CH₂CH₃ | CH₃ | Cl | Cl |
| 116 | OCH₂CH₂CH₃ | OCH₃ | Cl | Cl | for each respective pigment 91 through 116.

11. The pigment according to claim 8, wherein the pigment is nonmutagenic in accordance with the Ames test and the Prival modification of the Ames test.

12. The pigment according to claim 8, wherein the pigment exhibits a color selected from the group consisting of greenish-yellow, yellow, orange, red, brown, and combinations thereof.

13. A method of making a nonmutagenic pigment wherein the pigment has a formula selected from the group consisting of

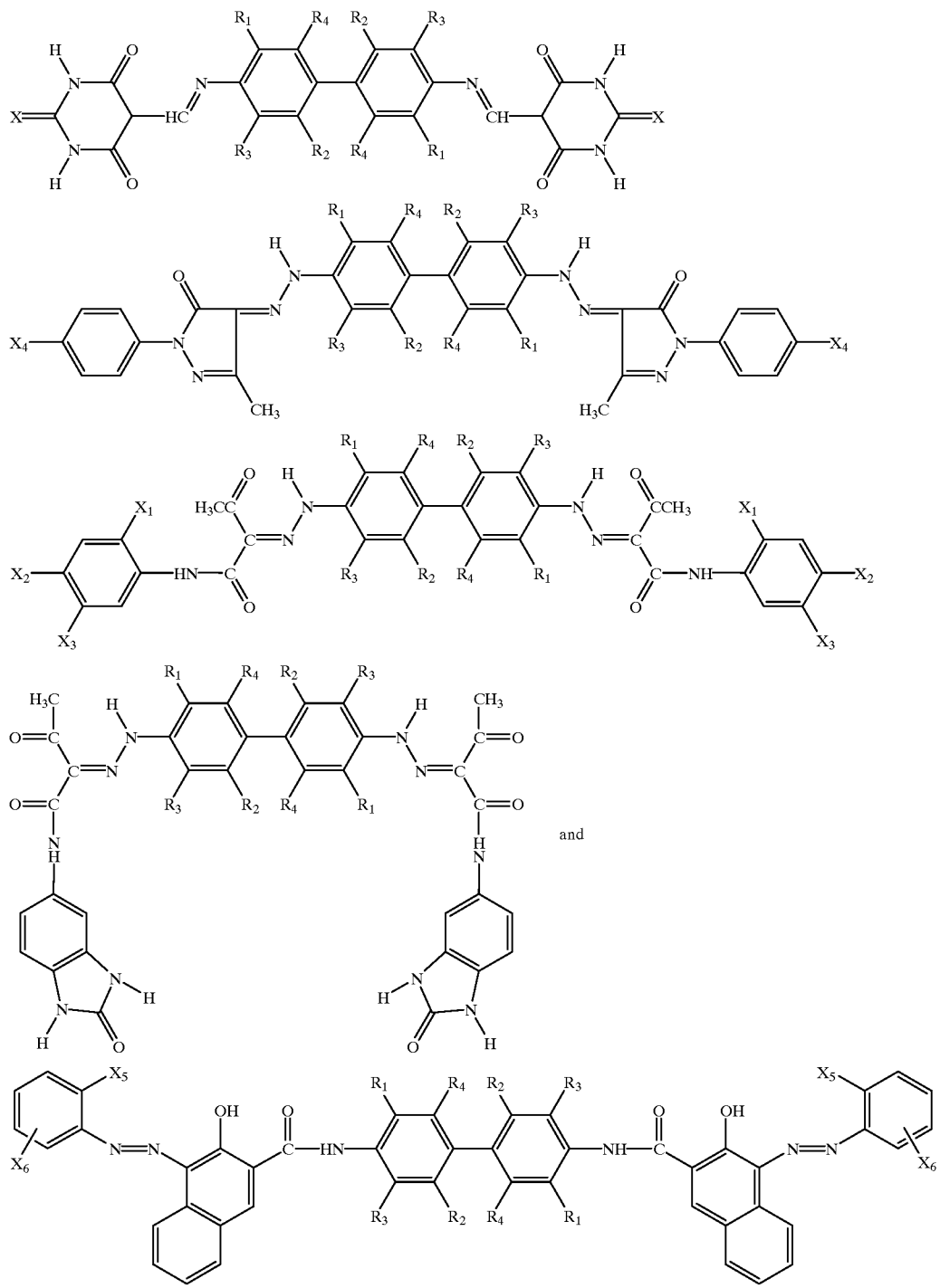

and wherein
each $R_1$ is the same and represents $C_{3-6}$-alkyl, $C_{3-6}$-alkoxy, $C_{3-6}$-hydroxyalkyl, $C_{3-6}$-alkoxyalkyl, or aryloxy, and
each $R_2$ is the same and represents halogen, $C_{1-4}$-alkyl, $C_{1-4}$-alkoxy, $C_{1-4}$-hydroxyalkyl, $C_{1-4}$-alkoxyalkyl, or aryloxy, and
each $R_3$ is the same and represents H or $CH_3$, and
each $R_4$ is the same and represents H, halogen, $C_{1-4}$-alkyl, $C_{1-4}$-alkoxy, $C_{1-4}$-hydroxyalkyl, $C_{1-4}$-alkoxyalkyl, or aryloxy, and
each X is the same and represents O, S, or NH, and
each $X_1$ is the same and represents H, $CH_3$, $OCH_3$, or halogen, and each $X_2$ is the same and represents H, $OCH_3$, or halogen, and
each $X_3$ is the same and represents H or halogen, and
each $X_4$ is the same and represents H or halogen, and
each $X_5$ is the same and represents H or halogen, and
each $X_6$ is the same and represents H or halogen,
said method comprising:
   a. providing a corresponding nonmutagenic, highly twisted benzidine compound or acid salts thereof, wherein the benzidine compound has the formula

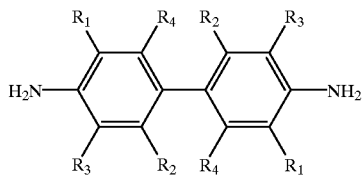

and the benzidine compound or acid salts thereof are correspondingly substituted with the same $R_1$, $R_2$, $R_3$, and $R_4$, and
   b. reacting the nonmutagenic benzidine compound or acid salts thereof with an agent, that substitutes on each N of the nonmutagenic benzidine compound or acid salts thereof, one of each of two of the same moieties, where each moiety has the same X, $X_1$, $X_2$, $X_3$, $X_4$, $X_5$, and $X_6$, and therefore that converts the nonmutagenic benzidine compound or acid salts thereof to the corresponding nonmutagenic pigment that is correspondingly substituted with the same $R_1$, $R_2$, $R_3$, $R_4$, X, $X_1$, $X_2$, $X_3$, $X_4$, $X_5$, and $X_6$.

14. The method of claim 13, wherein the formula is for bisazomethine pigments, and the agent is a formylating agent in the presence of an acid.

15. The method of claim 13, wherein the benzidine compound or acid salts thereof are first tetrazotized prior to reacting with the agent; and the formula is for pigments selected from the group consisting of disazoacetoacetanalides, disazopyrazolones, and disazobenzimidazolones; and the agent is a coupling agent selected from the group consisting of acetoacetanilide, 1-phenyl-3-methyl-5-pyrazolone, and 5-acetoacetylamino-benzimidazolone, respectively.

16. The method of claim 13, wherein the formula is for diazonaphthol pigments, and the agent is an aniline compound diazotized and coupled with 3-hydroxy-2-naphthoic acid followed by chlorination.

* * * * *